United States Patent [19]

Task

[11] Patent Number: 5,059,023
[45] Date of Patent: Oct. 22, 1991

[54] ANGULAR DEVIATION MEASUREMENT SYSTEM

[75] Inventor: Harry L. Task, Dayton, Ohio

[73] Assignee: The United States of America as represented by the Secretary of the Air Force, Washington, D.C.

[21] Appl. No.: 374,121

[22] Filed: Jun. 23, 1989

[51] Int. Cl.$^5$ ................ G01N 21/88; G01B 11/30
[52] U.S. Cl. .................................. 356/239; 356/371
[58] Field of Search .................. 356/73.1, 309, 320, 356/239, 351, 407, 414, 327

[56] References Cited

U.S. PATENT DOCUMENTS

| | | | |
|---|---|---|---|
| 3,025,749 | 3/1962 | Rodman et al. | 356/239 |
| 3,578,869 | 5/1971 | Irland et al. | 356/239 |
| 3,586,441 | 6/1971 | Smith et al. | 356/320 |
| 3,688,235 | 8/1972 | Migeotte | 356/239 |
| 3,792,930 | 2/1974 | Obenreder | 356/445 |
| 3,922,090 | 11/1975 | Fain | 356/407 |
| 3,972,616 | 8/1976 | Minami et al. | 356/71 |
| 4,249,823 | 2/1981 | Task | 356/128 |
| 4,309,106 | 1/1982 | Smith | 356/121 |
| 4,377,341 | 3/1983 | Task et al. | 356/239 |
| 4,398,822 | 8/1983 | Task | 356/239 |
| 4,453,827 | 6/1984 | Taboada | 356/353 |
| 4,632,554 | 12/1986 | Pearce | 356/351 |
| 4,732,483 | 3/1988 | Biegen | 356/351 |

Primary Examiner—Vincent P. McGraw
Assistant Examiner—LaCharles P. Keesee
Attorney, Agent, or Firm—Bobby D. Scearce; Donald J. Singer

[57] ABSTRACT

A system for measuring optical angular deviation in a transparency such as an aircraft or automobile windscreen, visor, optical lens or the like is described wherein orthogonal first and second incoherent light line images are combined and separately optically encoded, such as by wavelength or by polarization vector using suitable color or polarization filters or beamsplitters, and projected through a transparency under examination, the combined images then separated to detect simultaneously and separately the vertical and horizontal components of angular deviation at a specific location in the transparency.

6 Claims, 3 Drawing Sheets

ANGULAR DEVIATION MEASUREMENT SYSTEM

RIGHTS OF THE GOVERNMENT

The invention described herein may be manufactured and used by or for the government of the United States for all governmental purposes without the payment of any royalty.

BACKGROUND OF THE INVENTION

The present invention relates generally to systems for measuring optical distortion in transparencies, and more particularly to a system for measuring angular deviation in transparencies such as aircraft and automobile windscreens, visors and optical lenses.

Existing systems for measuring optical angular deviation in transparencies include those described in or referenced by U.S. Pat. No. 4,249,823, U.S. Pat. No. 4,377,341 and U.S. Pat. No. 4,398,822. Teachings of these patents and background material referenced therein are incorporated herein by reference without reiteration. A method finding substantial use and upon which an ASTM (American Society of Testing and Materials) standard test method is based utilizes the teachings of the '341 patent. In the '341 patent an incoherent light source illuminates a target in the form of an opaque slide with a transparent L-shaped pattern therein. Images of the legs of the L-shaped pattern are projected through a transparency under test to measure horizontal and vertical components of angular deviation characterizing the transparency. The method based on the '341 patent depends on geometric separation of the vertical and horizontal angular deviation components and results in horizontal and vertical angular deviation measurements at different locations on the transparency due to off-set effects of using an L-shaped pattern. The precise area of the transparency under test is therefore no easily determinable and resulting vignetting effects at the receiver lens of the system can lead to errors sufficiently significant to produce unacceptable results.

The invention described herein substantially solves or reduces in critical importance problems with existing systems for measuring angular deviation in transparencies by providing a system in which the vertical and horizontal components of angular deviation may be separated for independent simultaneous measurement at a specific locus of the transparency. Two fundamental nonlimiting approaches to separately optically encoding information on the orthogonal components are described. Certain embodiments include a dichroic beam splitter or set of color filters to project wavelength separated (e.g. red and green) crossed line images of a test beam through a transparency under test in order to examine separately the orthogonal components of angular deviation characterizing a specific area of the transparency. In another embodiment horizontal and vertical components of the test beam are encoded with different polarization vectors.

It is therefore a principal object of the invention to provide a system for measuring angular deviation in a transparency.

It is a further object of the invention to provide an angular deviation measurement system wherein both the horizontal and vertical angular deviation components are measured simultaneously for a specific portion of a transparency.

These and other objects of the invention will become apparent as the detailed description of representative embodiments proceeds.

SUMMARY OF THE INVENTION

In accordance with the foregoing principles and objects of the invention, a system for measuring optical angular deviation in a transparency such as an aircraft or automoblile windscreen, visor, optical lens or the like is described wherein orthogonal first and second incoherent light line images are combined and separately optically encoded, such as by wavelength or by polarization vector using suitable color or polarization filters or beamsplitters, and projected through a transparency under examination, the combined images then separated to detect simultaneously and separately the vertical and horizontal components of angular deviation in the transparency at a specific location in the transparency.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
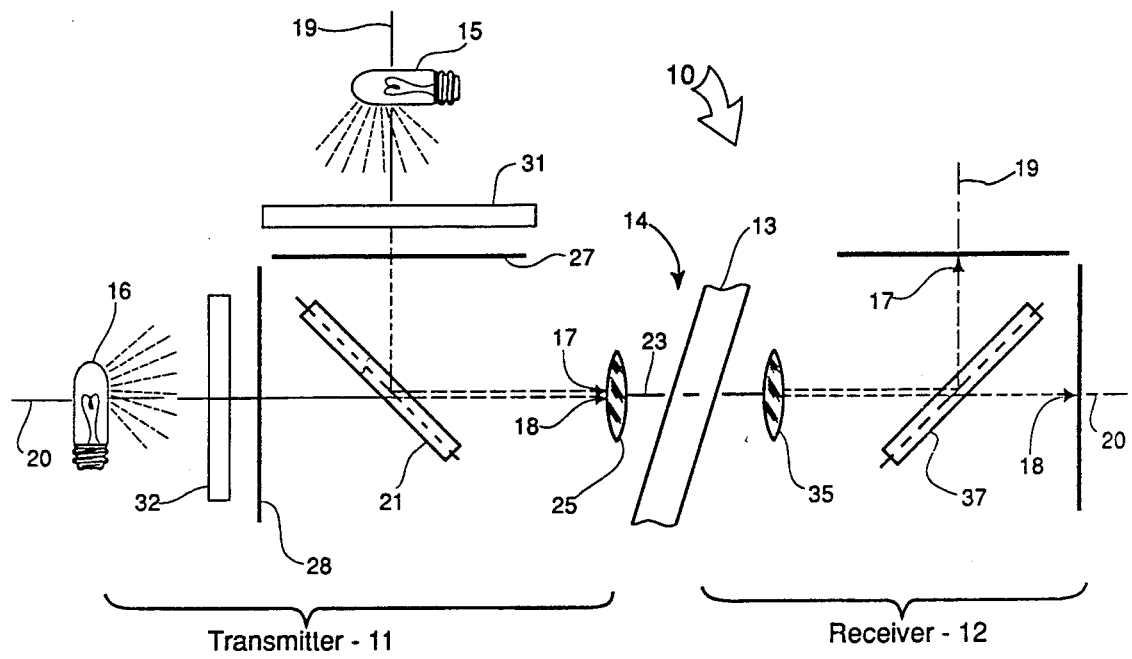
FIG. 1 is a schematic Plan view of a system for measuring optical angular deviation in a transparency according to the invention.
Figure 2:
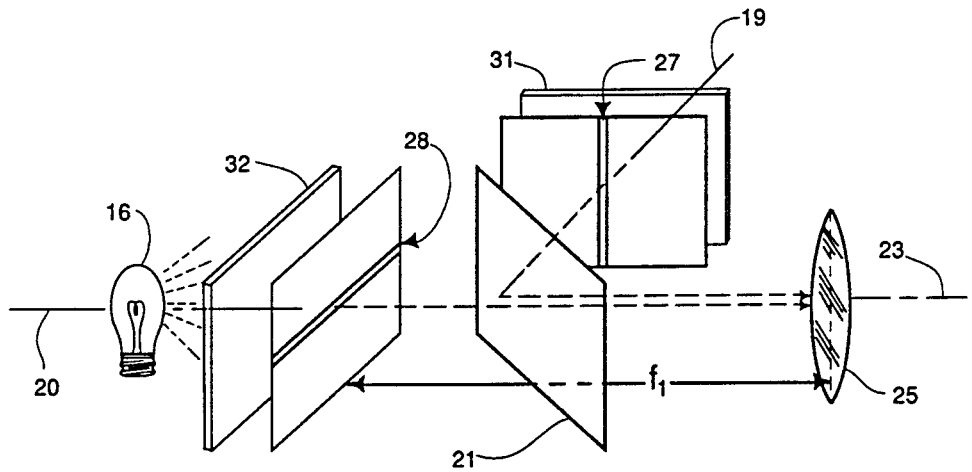
FIG. 2 is a schematic layout of the transmitter portion of the FIG. 1 system.
Figure 3:
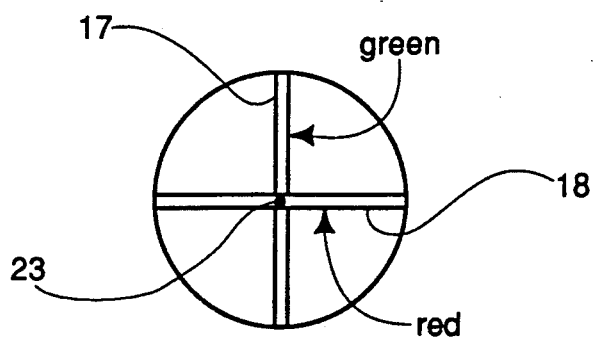
FIG. 3 is a representative view of the crossed line image projected by the transmitter portion of the FIG. 1 system.
Figure 4:
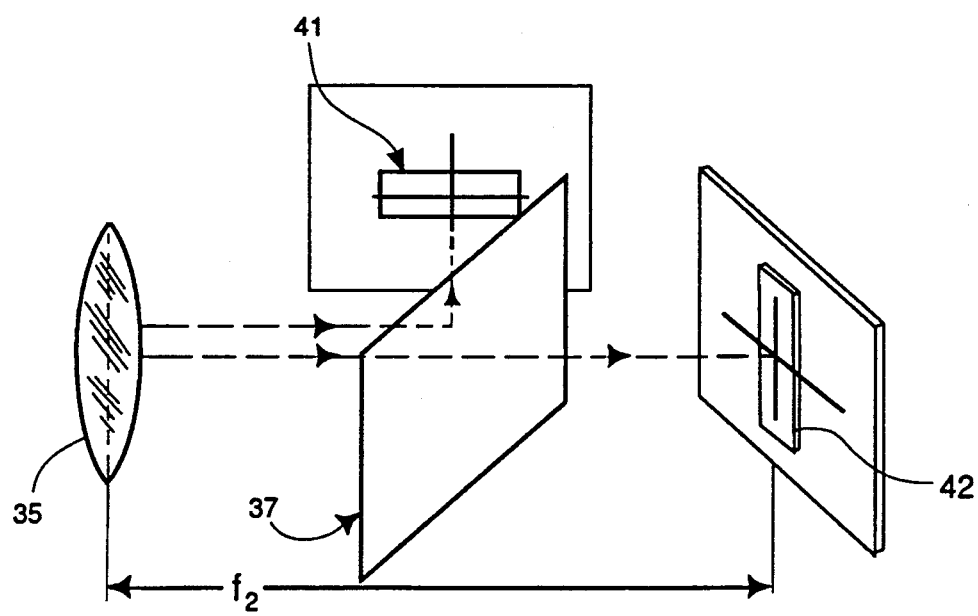
FIG. 4 is a schematic layout of the receiver portion of the FIG. 1 system.

Referring now to the drawings, FIG. 1 shows a schematic plan view of a representative system for measuring optical angular deviation in a transparency according to the invention. FIGS. 2 and 4 show schematically in somewhat more detail layouts of the transmitter and receiver portions of the FIG. 1 system. In the FIG. 1 embodiment, system 10 comprises a transmitter portion 11 and a receiver portion 12 between which a transparency 13 may be disposed within sample region 14 for examination in the practice of the invention. Transmitter portion 11 includes a pair of light sources 15,16 for projecting light beams 17,18 along respective optical axes 19,20 through sample region 14. Sources 15,16 are preferably substantially identical incandescent incoherent light sources each providing broad spectral emission, although a single source disposed in combination with suitable optics (not shown) for providing separate beams such as 17,18 may be used as would occur to one with skill in the field of the invention. Sources 15,16 may also be of separate (e.g. red and green) wavelengths the purpose of which will become apparent as the description of the invention continues. A dichroic beamsplitter 21 is disposed along both axes 19,20 substantially as shown, and has different reflectance and transmittance dependent on wavelength. For example, beamsplitter 21 may reflect green and transmit red which results, for the representative arrangement shown in FIGS. 1-4, in transmission along a common axis segment 23 of axes 19,20 and into projector lens 25 disposed therealong, a first spectral portion (e.g. green) of beam 17 and a second spectral portion (e.g. red) of beam 18. In an alternative embodiment of the invention, beamsplitter 21 (and a corresponding beamsplitter of receiver portion 12) may be a polarizing beamsplitter for imparting to beams 17,18, different polarization vectors. In yet further alternative embodiments of the invention described in more detail below with reference to FIG. 5, a set of polarizing filters or a set of color filters may be used as means to suitably optically encode beams 17,18 for projection along axis segment 23.

Referring now additionally to FIG. 2, a first spatial filter in the form of vertical slit 27 is disposed near one source 15 to define beam 17 as a first narrow, well-defined vertically aligned beam (e.g. encoded in green) as projected along axis segment 23. A second spatial filter in the form of horizontal slit 28 is disposed near the other source 16 to define beam 18 as a second narrow, well-defined, horizontally aligned beam (e.g. encoded in red) orthogonal to and intersecting beam 17. The crossed beam configuration assumed by spatially filtered and dichroically split beams 17,18 as projected along axis segment 23 and through projector lens 25 is shown in section in FIG. 3. Projector lens 25 is disposed one focal length ($f_1$) from each slit 27,28 and is representative of means for collimating crossed light beams 17,18 defined by crossed line images of slits 27,28 for projection of a crosshair-like image through transparency 13 in sample region 14.

Diffusers 31,32 may be disposed respectively between source 15 and slit 27 and between source 16 and slit 28 as suggested in FIGS. 1 and 2 to provide uniformity of illumination over the cross sections of each respective spatially filtered and dichroically split beam 17,18 as projected through sample region 14.

Referring now to FIG. 4 together with FIG. 1, receiver portion 12 of system 10 includes receiver lens 35 for capturing light in the form of crossed beams 17,18 projected through sample region 14 and transparency 13. Crossed beams 17,18 as received by receiver portion 12 are imaged through means, such as dichroic beamsplitter 37, for separating (decoding) encoded (green) beam 17 from the differently encoded (red) beam 18. The separate line images are projected along respective axes 19,20 onto separate optical detector 41,42 systems in order to examine the effect on the respective line images of slits 27,28 of transmission through transparency 13. The image planes of detectors 41,42 are each disposed one focal length ($f_2$) from lens 35 and may be in the form of respective linear charge coupled device (CCD) arrays 43,44. Other suitable detector systems for use in receiver portion 12 may include Photographic film, video camera, or linear diode position detector as would occur to the skilled artisan. In the embodiment shown, CCD array 43 is oriented horizontally for detecting the vertical (green) line image, and CCD array 44 is vertically disposed for detecting the horizontal (red) line image. The respective CCD arrays 43,44 and associated electronic circuitry connected thereto are configured to detect wherealong each array the respective line images fall, in manner substantially as described in U.S. Pat. No. 4,377,341 to Task et al and U.S. Pat. No. 4,309,106 to Smith referenced therein, the pertinent parts of both patents being incorporated here by reference. Given the spacing of CCD arrays 43,44 and the focal length $f_2$ of receiver lens 35, the angular deviation that each crossed beam 17,18 has experienced in traversing the thickness of transparency 13 may be calculated by comparison with equivalent null readings obtained with no transparency interposed within sample region 14.

If the CCD elements in each array 43,44 are spaced 0.001 inch apart and receiver lens 35 focal length $f_2$ is 10.0 inches, then the location (count) of each successive CCD element from the null position represents 0.1 milliradians of angular deviation. The presence and proper positioning of receiver lens 35 removes all effects of lateral displacement to ensure accurate readings. In addition, in the embodiment depicted in the drawings wherein chromaticity is used to encode the respective crossed beam 17,18 line images, the crosshair-like composite image may be accurately aligned with axis segment 23 coincident with the optical axis of receiver portion 12 to define with certainty that portion of transparency 13 which is being measured. In order to minimize vignetting effects, projector lens 25 may be made smaller in diameter than receiver lens 35 to ensure that substantially all light transmitted by transmitter portion 11 is captured for measurement at receiver portion 12.

Figure 5:
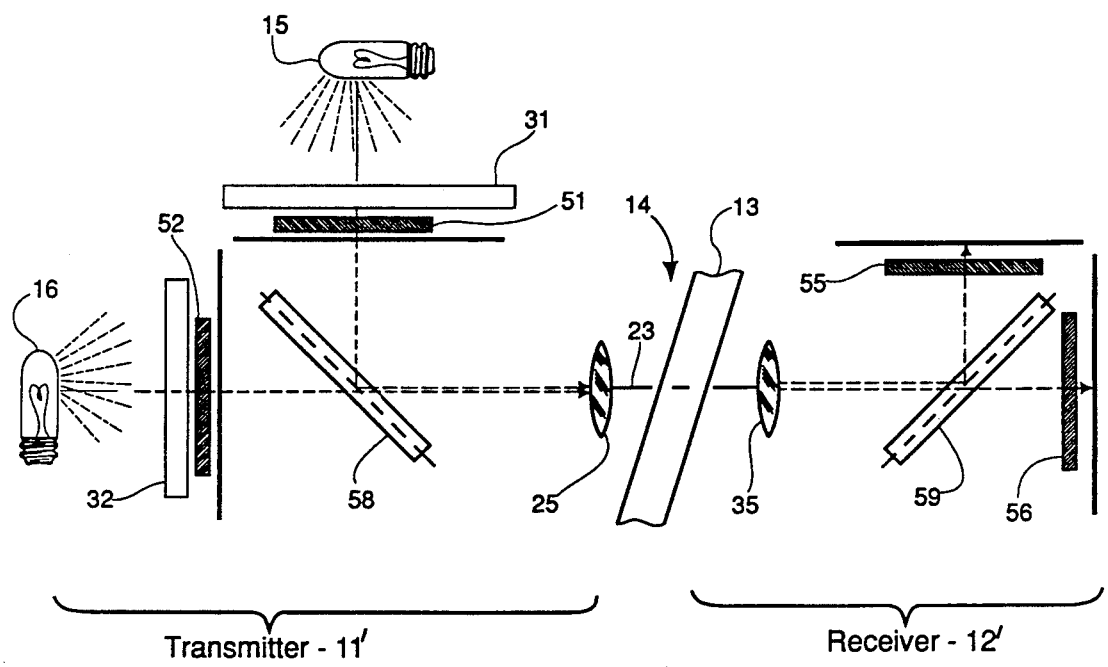
FIG. 5 is a schematic plan view illustrating alternative embodiments of the invention for encoding the crossed line images for projection through the transparency to be examined.

Referring now to FIG. 5, illustrated therein are alternative embodiments of the invention utilizing alternate means to encode the crossed line images for projection through a transparency under test. In one alternative embodiment, suitable filters 51,52 may be interposed along respective optical axes 19,20 to provide the desired wavelength encoding to beams 17,18 projected through transparency 13. Corresponding color filters 55,56 are disposed near detectors 41,42 as suggested in FIG. 5 to decode the projected sample affected beams 17,18. In this arrangement, beamsplitter 58 in transmitter portion 11' and beamsplitter 59 in receiver portion 12' are ordinary neutral beamsplitters instead of the dichroic type included in the FIG. 1 embodiment. As a further alternative, filters 51,52 may be polarizing filters to impart to respective beams 17,18 different polarization characteristics, and filters 55,56 are of the corresponding type for discriminating the two orthogonal line images transmitted through transparency 13.

The invention therefore provides an angular deviation measurement system wherein orthogonal angular deviation components may be measured simultaneously for a specific portion of a transparency. It is understood that modifications to the invention may be made as might occur to one with skill in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

I claim:
1. A system for measuring angular deviation in a transparency, comprising:
   (a) a source of incoherent light;
   (b) means for projecting first and second light beams from said source, and spatial filter means for defining said first and second light beams as crossed respective first and second line images of said source, and for directing said first and second beams along an optical axis through a sample region;
   (c) encoding means disposed along said optical axis between said source and said sample region for encoding said first and second light beams with respective different optical characteristics;

(d) collimating means disposed along said optical axis between said encoding means and said sample region for collimating said first and second light beams for projection thereof through said sample region as respective first and second projected sample beams;

(e) first and second optical detectors;

(f) means for receiving said first and second projected sample beams and for focusing said first and second projected sample beams onto respective said first and second optical detectors; and (g) decoding means disposed between said focusing means and said respective first and second optical detectors for separating the projected first beam from the projected second beam for projection onto respective said first and second optical detectors, for detecting shifts in positions of respective said first and second line images resulting from angular deviation characteristic of a specific area of a transparency disposed in said sample region.

2. The system of claim 1 wherein said encoding means and said decoding means include substantially identical dichroic beamsplitters.

3. The system of claim 1 wherein said encoding means and said decoding means include substantially identical polarizing beamsplitters.

4. The system of claim 1 wherein said encoding means includes respective separate first and second color filters and a neutral beamsplitter for combining said first and second light beams, and said decoding means includes corresponding respective third and fourth color filters and a neutral beamsplitter for separating said first and second projected sample beams.

5. The system of claim 1 wherein said encoding means includes respective separate first and second polarizing filters and a neutral beamsplitter for combining said first and second light beams, and said decoding means includes corresponding respective third and fourth polarizing filters and a neutral beamsplitter for separating said first and second projected sample beams.

6. The system of claim 1 wherein said collimating means includes a collimating lens, said receiving means includes a focusing lens, and said first and second optical detectors comprise first and second linear charge coupled device arrays, each said first and second linear charge coupled device arrays being disposed at a focal plane of said focusing lens.

* * * * *